(12) United States Patent
Shimauchi et al.

(10) Patent No.: US 10,607,631 B2
(45) Date of Patent: Mar. 31, 2020

(54) SIGNAL FEATURE EXTRACTION APPARATUS, SIGNAL FEATURE EXTRACTION METHOD, AND PROGRAM

(71) Applicant: NIPPON TELEGRAPH AND TELEPHONE CORPORATION, Chiyoda-ku (JP)

(72) Inventors: Suehiro Shimauchi, Musashino (JP); Kana Eguchi, Yokosuka (JP); Tsutomu Yabuuchi, Yokosuka (JP); Kazuhiro Yoshida, Yokosuka (JP); Osamu Mizuno, Musashino (JP)

(73) Assignee: NIPPON TELEGRAPH AND TELEPHONE CORPORATION, Chiyoda-ku (JP)

( * ) Notice: Subject to any disclaimer, the term of this patent is extended or adjusted under 35 U.S.C. 154(b) by 0 days.

(21) Appl. No.: 16/464,751

(22) PCT Filed: Dec. 5, 2017

(86) PCT No.: PCT/JP2017/043656
§ 371 (c)(1),
(2) Date: May 29, 2019

(87) PCT Pub. No.: WO2018/105614
PCT Pub. Date: Jun. 14, 2018

(65) Prior Publication Data
US 2019/0385631 A1 Dec. 19, 2019

(30) Foreign Application Priority Data

Dec. 6, 2016 (JP) .................... 2016-236591

(51) Int. Cl.
*G10L 25/18* (2013.01)
*G10L 25/51* (2013.01)
*H04R 3/04* (2006.01)

(52) U.S. Cl.
CPC .............. *G10L 25/18* (2013.01); *G10L 25/51* (2013.01); *H04R 3/04* (2013.01)

(58) Field of Classification Search
CPC ........... G10L 25/18; G10L 25/51; H04R 3/04; H04R 3/00; H04R 29/00; H04R 29/001;
(Continued)

(56) References Cited

U.S. PATENT DOCUMENTS 6,308,155 B1 * 10/2001 Kingsbury .............. G10L 15/02
704/231
7,440,892 B2 * 10/2008 Tamura ................... G10L 21/02
704/205
(Continued)

OTHER PUBLICATIONS

International Search Report dated Jan. 23, 2018 in PCT/JP2017/043656 filed Dec. 5, 2017.
(Continued)

*Primary Examiner* — Ahmad F. Matar
*Assistant Examiner* — Sabrina Diaz
(74) *Attorney, Agent, or Firm* — Oblon, McClelland, Maier & Neustadt, L.L.P.

(57) ABSTRACT

The purpose of the present invention is to reduce leakage of an output signal between band-pass filters and in the time axis direction. A signal input part 1 vectorizes an input signal x(n). An extended impulse response matrix generation part 2 generates an extended impulse response matrix $H_e$ in which impulse response vectors using impulse response sequences of band-pass filters as elements are extended in the time axis direction. An expansion coefficient calculation part 3 calculates an expansion coefficient vector $\hat{y}(n)$ using an input signal vectors $\overline{x}(n)$ and the extended impulse response matrix $H_e$. A signal output part 4 outputs at least one of expansion coefficients corresponding to a center vector of the extended impulse response matrix $H_e$ of the expansion coefficient vector $\hat{y}(n)$.

7 Claims, 5 Drawing Sheets

(58) Field of Classification Search
CPC ...... H04R 29/004; H04R 27/00; H03G 5/165; H03G 5/005; H03G 5/025; H04S 7/307; H04S 7/301
USPC ..................................................... 381/58, 98
See application file for complete search history.

(56) References Cited

U.S. PATENT DOCUMENTS

| | | | |
|---|---|---|---|
| 9,058,807 B2* | 6/2015 | Tamura | G10L 13/04 |
| 10,090,005 B2* | 10/2018 | Rumberg | G10L 25/81 |
| 2002/0010583 A1* | 1/2002 | Iwahashi | G10L 15/20 |
| | | | 704/255 |
| 2007/0060827 A1* | 3/2007 | Kobayashi | A61B 5/02416 |
| | | | 600/500 |

OTHER PUBLICATIONS

Vetterli, M. et al., "Wavelets and Filter Banks: Theory and Design," IEEE Transactions on Signal Processing, vol. 40, No. 9, Sep. 1992, pp. 2207-2232.

* cited by examiner

SIGNAL FEATURE EXTRACTION APPARATUS, SIGNAL FEATURE EXTRACTION METHOD, AND PROGRAM

TECHNICAL FIELD

The present invention relates to a technique for extracting features of a signal waveform of an acoustic signal, a biological signal, or the like.

BACKGROUND ART

As a signal feature extraction technique for analyzing features of an acoustic signal, a biological signal, or the like, there is analysis by a filter bank composed of a group of band-pass filters having different center frequencies and band widths (for example, see non-patent literature 1).

Figure 1:
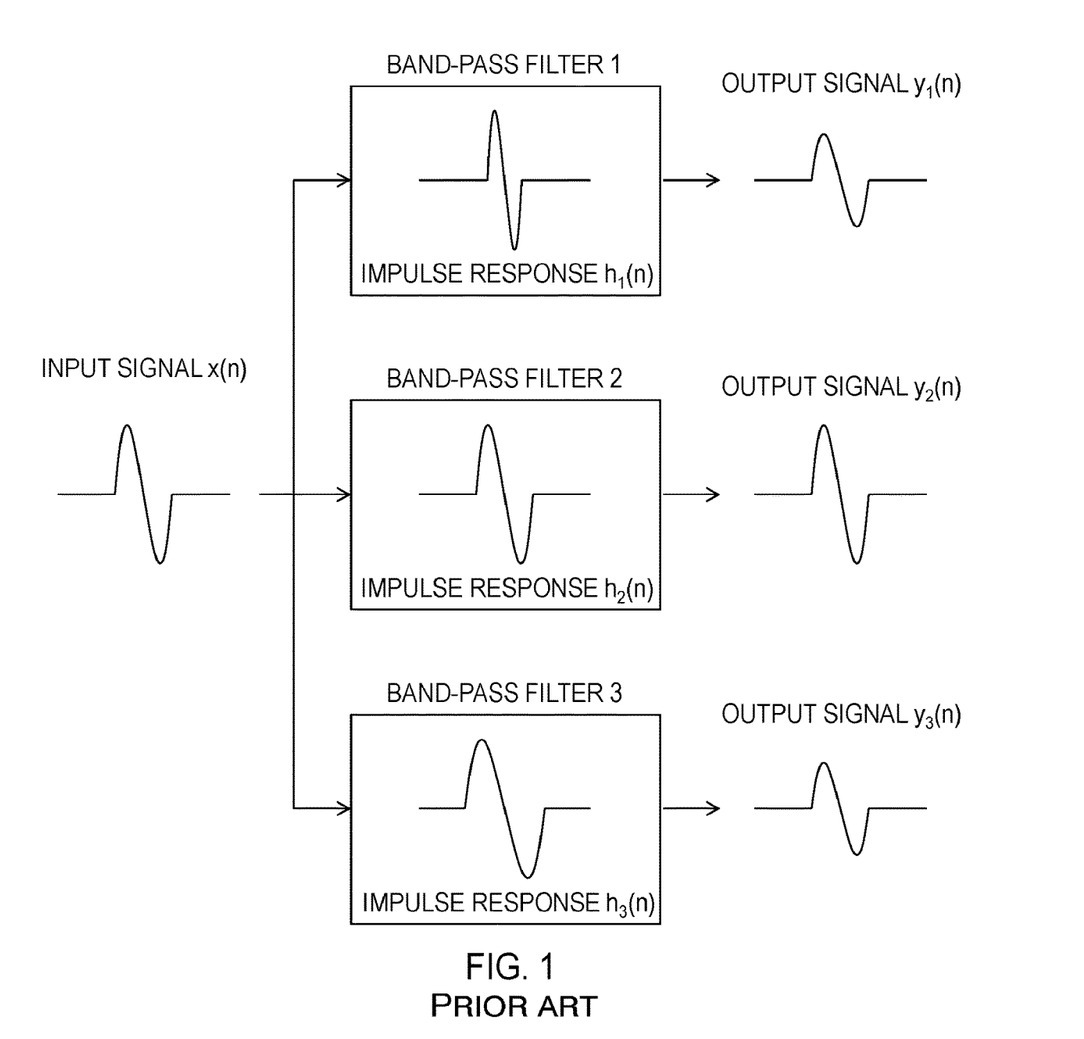
FIG. 1 is a diagram for illustrating conventional filter bank processing.

FIG. 1 schematically illustrates a processing flow of the filter bank. Here, a filter bank that applies three band-pass filters 1-3 to an input signal $x(n)$ is considered. It is assumed that the filter bank is designed to match a specific input signal pattern to an impulse response of a specific band-pass filter. In an example of FIG. 1, a waveform pattern of the input signal $x(n)$ is substantially the same shape as an impulse response $h_2(n)$ of the band-pass filter 2, and it is expected that only an output signal $y_2(n)$ of the band-pass filter 2 takes a large output value in response to the waveform pattern of the input signal $x(n)$ compared among the output of the band-pass filters 1-3.

PRIOR ART LITERATURE

Non-Patent Literature

Non-patent literature 1: M. Vetterli and C. Herley, "Wavelets and filter banks: theory and design," in IEEE Transactions on Signal Processing, vol. 40, no. 9, pp. 2207-2232, September 1992.

SUMMARY OF THE INVENTION

Problems to be Solved by the Invention

In the filter bank analysis, because bands of respective band-pass filters overlap, features of a signal leak out to outputs of a plurality of adjacent filters, and analysis results may be redundant in some cases. In the example of FIG. 1, it is expected that only the output signal $y_2(n)$ of the band-pass filter 2 takes a large output value, but actually the waveform pattern of the input signal $x(n)$ also leaks out to output signals $y_1(n)$ and $y_3(n)$ of the adjacent band-pass filters 1 and 3, which may make it difficult to analyze filter bank outputs.

An object of the present invention is to provide a signal feature extraction technique that can reduce leakage of an output signal to adjacent band-pass filters and in a time axis direction in filter bank analysis and flexibly cope with diversity of feature patterns of input signals to be analyzed.

Means to Solve the Problems

In order to solve the above-described problem, a signal feature extraction apparatus of a first aspect of the present invention is a signal feature extraction apparatus that extracts features of an input signal by filter bank analysis including a plurality of band-pass filters, assuming that M denotes a number of the band-pass filters, L denotes an integer which a maximum value of impulse response length of the band-pass filters is $2L+1$, m denotes each integer from 1 or more to M or less, k denotes each integer from $-2L$ or more to $2L$ or less, $z_k$ denotes a column vector having $|k|$ zeros as elements, $\overline{x}(n)=[x(n+L), \ldots, x(n+1), x(n), x(n-1), \ldots, x(n-L)]^H$ denotes an input signal vector having an input signal sequence at time n as elements, and $\overline{h}_m = [h_m(-L), \ldots, h_m(-1), h_m(0), h_m(+1), \ldots, h_m(L)]^H$ denotes an impulse response vector having an impulse response sequence of an m-th band-pass filter as elements, the signal feature extraction apparatus including: an extended impulse response matrix generation part that generates an extended impulse response matrix $H_e$ expressed by a following formula $$H_e = [\overline{h}_{1,-2L}, \ldots, \overline{h}_{1,2L}, \ldots, \overline{h}_{m,-2L}, \ldots, \overline{h}_{m,2L}, \ldots, \overline{h}_{M,-2L}, \ldots, \overline{h}_{M,2L}]$$

using an impulse response sequence $\overline{h}_{m,k}$ which is, when $k<0$, $$\overline{h}_{m,k} = [h_m(-L-k), \ldots, h_m(-1), h_m(0), h_m(1), \ldots, h_m(L), z_k^H]^H,$$

and when $k \geq 0$, $$\overline{h}_{m,k} = [z_k^H, h_m(-L), \ldots, h_m(-1), h_m(0), h_m(1), \ldots, h_m(L-k)]^H,$$

an expansion coefficient calculation part that obtains an expansion coefficient vector $\hat{y}(n)$ by calculating a following formula $$\hat{y}(n) = \underset{\overline{y}(n)}{\operatorname{argmax}}(\|\overline{x}(n) - H_e \overline{y}(n)\|_2^2 + \lambda \|\overline{y}(n)\|_1)$$

using the input signal vector $\overline{x}(n)$ and the extended impulse response matrix $H_e$; and a signal output part that outputs as an output signal at least one of expansion coefficients corresponding to a center impulse response vector $\overline{h}_{m,0}$ of the extended impulse response matrix $H_e$ of the expansion coefficient vector $\hat{y}(n)$.

A signal feature extraction apparatus of a second aspect of the present invention is a signal feature extraction apparatus that extracts features of an input signal by filter bank analysis including a plurality of band-pass filters, assuming that a superscript H denotes transposition, M denotes a number of the band-pass filters, L denotes a value which a maximum value of impulse response length of the band-pass filters is $2L+1$, m denotes each integer from 1 or more to M or less, k denotes each integer from $-2L$ or more to $2L$ or less, $z_k$ denotes a column vector having $|k|$ zeros as elements, $\overline{x}(n)=[x(n+L), \ldots, x(n+1), x(n), x(n-1), \ldots, x(n-L)]^H$ denotes an impulse signal vector having an input signal sequence at time n as elements, and $\overline{h}_m=[h_m(-L), \ldots, h_m(-1), h_m(0), h_m(+1), \ldots, h_m(L)]^H$ denotes an input response vector having an impulse response sequence of an m-th band-pass filter as elements, the signal feature extraction apparatus including: an extended impulse response matrix generation part that generates an extended impulse response matrix $H_c$ by extracting predetermined column vectors from an extended impulse response matrix $H_e$ expressed by a following formula $$H_e = [\overline{h}_{1,-2L}, \ldots, \overline{h}_{1,2L}, \ldots, \overline{h}_{m,-2L}, \ldots, \overline{h}_{m,2L}, \ldots, \overline{h}_{M,-2L}, \ldots, \overline{h}_{M,2L}]$$

generated by using an impulse response sequence $-h_{m,k}$ which is, when $k<0$, $$\bar{h}_{m,k}=[h_m(-L-k),\ldots,h_m(-1),h_m(0),h_m(1),\ldots,h_m(L),z_k^H]^H,$$

and when $k \geq 0$, $$\bar{h}_{m,k}=[z_k^H,h_m(-L),\ldots,h_m(-1),h_m(0),h_m(1),\ldots,h_m(L-k)]^H,$$

an expansion coefficient calculation part that obtains an expansion coefficient vector ˆy(n) by calculating a following formula $$\hat{y}(n)=[H_c^H H_c]^{-1}H_c^H \bar{x}(n)$$

using the input signal vector ⃗x(n) and the extended impulse response matrix $H_c$; and a signal output part that outputs as an output signal at least one of expansion coefficients corresponding to a center impulse response vector ⃗$h_{m,0}$ of the extended impulse response matrix $H_c$ of the expansion coefficient vector ˆy(n).

Effects of the Invention

According to the signal feature extraction technique of the invention, it is possible to reduce leakage of an output signal between adjacent band-pass filters and in the time axis direction on filter bank analysis and flexibly cope with diversity of feature patterns of input signals to be analyzed.

DETAILED DESCRIPTION OF THE EMBODIMENTS

Symbols "⁓", "ˆ", "⎯", and the like used herein should be written directly above an immediately following character, but due to restriction of text notation, they are written immediately before the character. In formulas, the symbols are written at their original position, that is, directly above the character.

Figure 2:
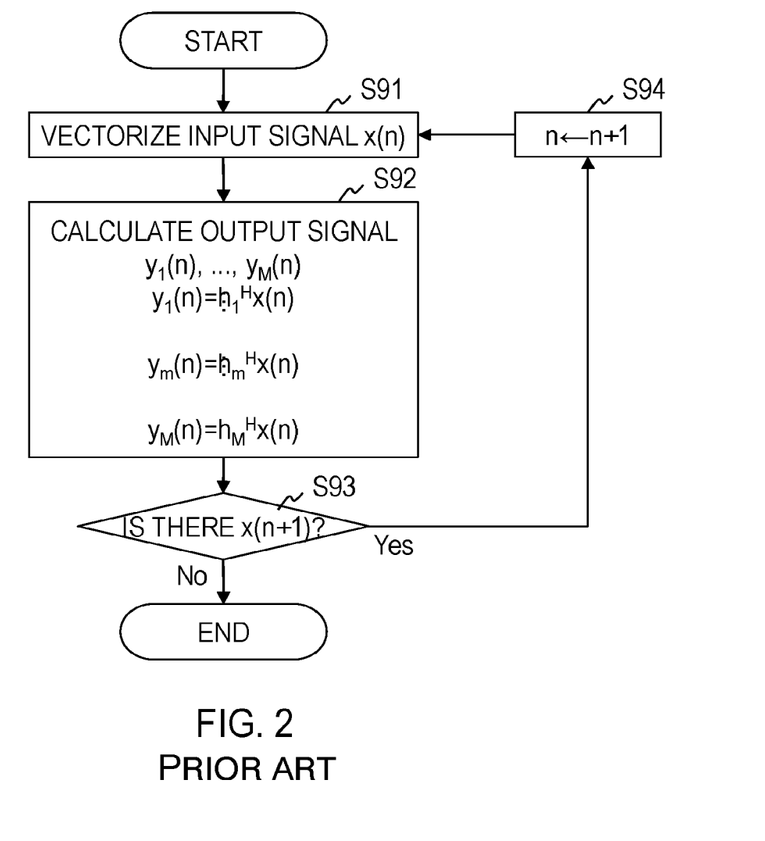
FIG. 2 is a diagram exemplifying a processing procedure of a signal feature extraction method of the prior art.

A processing flow of a signal feature extraction method based on conventional filter bank analysis is shown in FIG. 2. The conventional filter bank analysis uses an input signal vector to be analyzed denoted as ⃗x(n)=[x(n+L), ..., x(n+1), x(n), x(n−1), ..., x(n−L)]$^H$ having a signal sequence centering around a certain time n as elements and an impulse response vector ⃗$h_m$=[$h_m$(−L), ..., $h_m$(−1), $h_m$(0), $h_m$(+1), ..., $h_m$(L)]$^H$ having an impulse response sequence of an m-th band-pass filter as elements to calculate an output signal $y_m$(n) of the m-th band-pass filter by either multiply-add operation represented by a formula (1) or filter processing calculation equivalent to it.

$$y_m(n)=\bar{h}_m^H \bar{x}(n) \quad (1)$$

In the above formula, $^H$ (superscript H) denotes transpose of a vector or matrix, and when its elements are complex numbers, it denotes conjugate transpose. The maximum value of impulse response length of each band-pass filter is assumed to be 2L+1. Regarding m, it is any integer of 1 or more and M or less. Regarding M, it is the total number of the band-pass filters. There is a case where the impulse response length is different depending on the identification number in of band-pass filter, and some elements of an impulse response vector ⃗$h_m$ related to a band-pass filter become 0 when impulse response length is less than 2L+1. In that case, multiply-add operation of the formula (1) of a part where an element is 0 can be omitted.

One of reasons why leakage occurs in the output between adjacent band-pass filters in the above-described prior art is that pass bands of the adjacent band-pass filters are generally designed to overlap with each other. Considering a fact that an output signal is independently calculated for each band-pass filter in accordance with the formula (1) in the conventional filter bank is regarded as one of the reasons for leakage, a filter bank in the invention is configured in consideration of a mutual influence of band-pass filters.

For example, in FIG. 1, it is considered representing the input signal vector ⃗x(n) by a linear combination of impulse response vectors ⃗$h_1$, ⃗$h_2$, and ⃗$h_3$ of the respective filter banks. That is, it gives a relationship that satisfies a formula (2).

$$\bar{x}(n) = \alpha_1 \bar{h}_1 + \alpha_2 \bar{h}_2 + \alpha_3 \bar{h}_3 = H \begin{bmatrix} \alpha_1 \\ \alpha_2 \\ \alpha_3 \end{bmatrix}, \quad (2)$$

where, $$H=[\bar{h}_1 \bar{h}_2 \bar{h}_3] \quad (3).$$

In the example of FIG. 1, because it considers a case where the input signal ⃗x(n) has a waveform pattern of a shape equal to the impulse response ⃗$h_2$, that is ⃗x(n)=⃗$h_2$, expansion coefficients $\alpha_1$, $\alpha_2$, and $\alpha_3$ should be given like a formula (4).

$$\begin{bmatrix} \alpha_1 \\ \alpha_2 \\ \alpha_3 \end{bmatrix} = \begin{bmatrix} 0 \\ 1 \\ 0 \end{bmatrix} \quad (4)$$

Such expansion coefficients are given as least-squares solutions of a formula (5) if 2L+1>3 is satisfied.

$$\begin{bmatrix} \alpha_1 \\ \alpha_2 \\ \alpha_3 \end{bmatrix} = [H^H H]^{-1} H^H \bar{x}(n) \quad (5)$$

Here, it is assumed that the expansion coefficients $\alpha_1$, $\alpha_2$, and $\alpha_3$ correspond to output signals at the time n, and it is considered that they are allocated like a formula (6).

$$\begin{bmatrix} y_1(n) \\ y_2(n) \\ y_3(n) \end{bmatrix} = \begin{bmatrix} \alpha_1 \\ \alpha_2 \\ \alpha_3 \end{bmatrix} = [H^H H]^{-1} H^H \bar{x}(n) \quad (6)$$

As a result, in the example of FIG. 1, a formula (7) is obtained, and leakage to the adjacent band-pass filters is prevented.

$$\begin{bmatrix} y_1(n) \\ y_2(n) \\ y_3(n) \end{bmatrix} = \begin{bmatrix} 0 \\ 1 \\ 0 \end{bmatrix} \quad (7)$$

On the other hand, outputs of the conventional band-pass filters are represented by a formula (8), which is different from the formula (6).

$$\begin{bmatrix} y_1(n) \\ y_2(n) \\ y_3(n) \end{bmatrix} = H^H \overline{x}(n) \quad (8)$$

In this case, even in the example of FIG. 1, results of the formula (7) are not obtained, and leakage to the adjacent band-pass filters occurs.

Because the input signal vector $\overline{\phantom{x}}x(n)$ is time series data varying over time, output signals obtained for an input signal vector $\overline{\phantom{x}}x(n+1)$ which is shifted by one sample become like a formula (9)

$$\begin{bmatrix} y_1(n+1) \\ y_2(n+1) \\ y_3(n+1) \end{bmatrix} = \begin{bmatrix} \alpha_1 \\ \alpha_2 \\ \alpha_3 \end{bmatrix} = [H^H H]^{-1} H^H \overline{x}(n+1) \quad (9)$$

Although the input signal vector $\overline{\phantom{x}}x(n+1)$ no longer coincides with any of the impulse response vectors $\overline{\phantom{x}}h_1$, $\overline{\phantom{x}}h_2$, and $\overline{\phantom{x}}h_3$ including the time axis, output signals $y_1(n+1)$, $y_2(n+1)$, and $y_3(n+1)$ take non-zero values. That is, leakage to the time axis direction cannot be prevented. Therefore, there is further considered an impulse response sequence $\overline{\phantom{x}}h_{m,k}$ that is time shifted and becomes a formula (10) when k<0, and becomes a formula (11) when k≥0 for k=−2L, . . . , −1, 0, 1, . . . , 2L.

$$\overline{h}_{m,k} = [h_m(-L-k), \ldots, h_m(-1), h_m(0), h_m(1), \ldots, h_m(L), z_k^H]^H \quad (10)$$

$$\overline{h}_{m,k} = [z_k^H, h_m(-L), \ldots, h_m(-1), h_m(0), h_m(1), \ldots, h_m(L-k)]^H \quad (11)$$

In the above, $z_k$ denotes a column vector having |k| zeros as elements. It is assumed that these impulse response sequences are given as complex number sequences, sequences of real part and imaginary part can be mutually converted by Hilbert transformation or have an approximate equivalent relationship. It is considered extending the impulse response matrix H of the formula (3) to an extended impulse response matrix $H_e$ of $(2L+1) \times M(4L+1)$ shown in a formula (12) and obtain an output signal from an expansion coefficient vector $\overline{\phantom{y}}y(n)$ satisfying a formula (13).

$$H_e = [\overline{h}_{1,-2L}, \ldots, \overline{h}_{1,2L}, \ldots, \overline{h}_{m,-2L}, \ldots, \overline{h}_{m,2L}, \ldots, \overline{h}_{M,-2L}, \ldots, \overline{h}_{M,2L}] \quad (12)$$

$$\overline{x}(n) = H_e \overline{y}(n) \quad (13)$$

However, in the formula (13), the number of elements of the expansion coefficient vector $\overline{\phantom{y}}y(n)$ which is an unknown number is $M(4L+1)$, and because it exceeds the number $(2L+1)$ of the equation, it becomes an indefinite problem of inferior determination. Therefore, it is impossible to uniquely obtain least-squares solutions in the same manner as the formula (6). Therefore, a solution by which a value of L1 norm $\|\overline{\phantom{y}}y(n)\|_1$ is the minimum or a sufficiently small value among indefinite solutions is obtained by, for example, a lasso method and the following sparse solution $\hat{y}(n)$ is obtained.

$$\hat{y}(n) = \underset{\overline{y}(n)}{\operatorname{argmax}} (\|\overline{x}(n) - H_e \overline{y}(n)\|_2^2 + \lambda \|\overline{y}(n)\|_1) \quad (14)$$

In the above, $\lambda$, is a positive constant called a regularization parameter.

What are actually used as output signals are only values $\hat{y}_1(n), \ldots, \hat{y}_m(n), \ldots, \hat{y}_m(n)$ of expansion coefficients corresponding to center impulse response vectors $\overline{\phantom{h}}h_{1,0}, \ldots, \overline{\phantom{h}}h_{m,0}, \ldots, \overline{\phantom{h}}h_{M,0}$ which are not shifted, and further limited to only expansion coefficients corresponding to impulse responses having specific patterns of interest among the center impulse response vectors $\overline{\phantom{h}}h_{1,0}, \ldots, \overline{\phantom{h}}h_{m,0}, \ldots, \overline{\phantom{h}}h_{M,0}$. For example, if the input signal vector $\overline{\phantom{x}}x(n)$ coincides with any of the center impulse response vectors $\overline{\phantom{h}}h_{1,0}, \ldots, \overline{\phantom{h}}h_{m,0}, \ldots, \overline{\phantom{h}}h_{M,0}$ and the corresponding expansion coefficient takes a large value, the expansion coefficients for the input signal vector $\overline{\phantom{x}}x(n+1)$ which is shifted by one sample take a large value for the center impulse response vectors $\overline{\phantom{h}}h_{1,1}, \ldots, \overline{\phantom{h}}h_{m,1}, \ldots, \overline{\phantom{h}}h_{M,1}$ that are actually not output, but take a small value for the center impulse response vectors $\overline{\phantom{h}}h_{1,0}, \ldots, \overline{\phantom{h}}h_{m,0}, \ldots, \overline{\phantom{h}}h_{M,0}$ which are actually output, and therefore leakage to the time axis direction can be also prevented.

Embodiments of the present invention will be described below in detail. Constituent parts having the same functions are given the same identification numbers in the drawings and redundant explanation will be omitted.

First Embodiment

Figure 3:
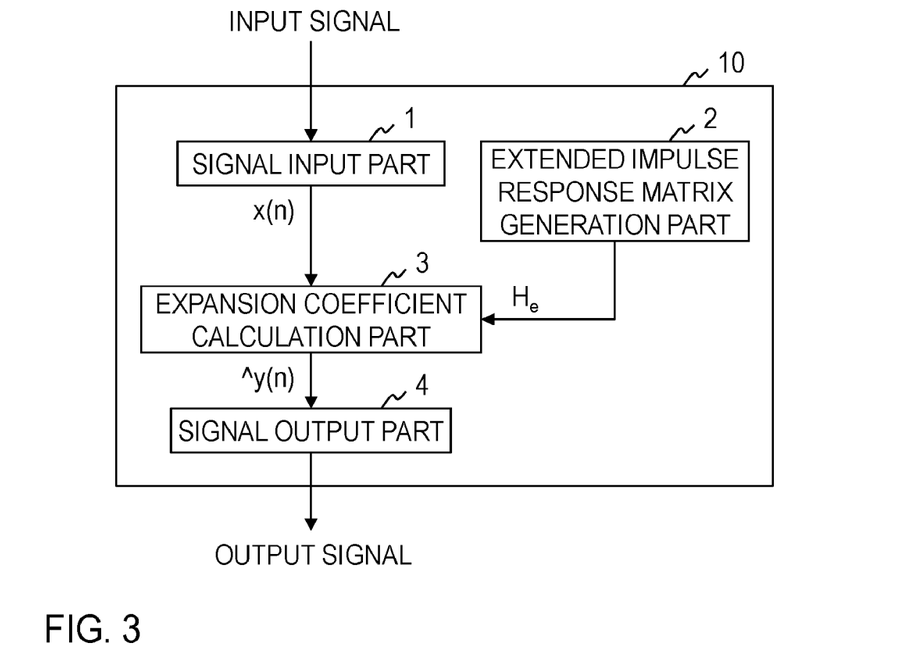
FIG. 3 is a diagram exemplifying a functional configuration of a signal feature extraction apparatus.

A signal feature extraction apparatus 10 of a first embodiment includes a signal input part 1, an extended impulse response matrix generation part 2, an expansion coefficient calculation part 3, and a signal output part 4 as shown in FIG. 3. The signal feature extraction apparatus 10 performs processing of steps shown in FIG. 4 and thereby implements a signal feature extraction method of the first embodiment.

The signal feature extraction apparatus 10 is a special apparatus formed, for example, by causing a known or dedicated computer including a central processing unit (CPU), main storage device (RAM: Random Access Memory), and the like to read in a special program. The signal feature extraction apparatus 10 performs the processing, for example, under control of the central processing unit. Data input into the signal feature extraction apparatus 10 or data obtained by the processing is stored, for example, in the main storage device, and the data stored in the main storage device is read out on demand, and used for other processing. At least part of processing parts of the signal feature extraction apparatus 10 may be configured by hardware such as an integrated circuit.

Figure 4:
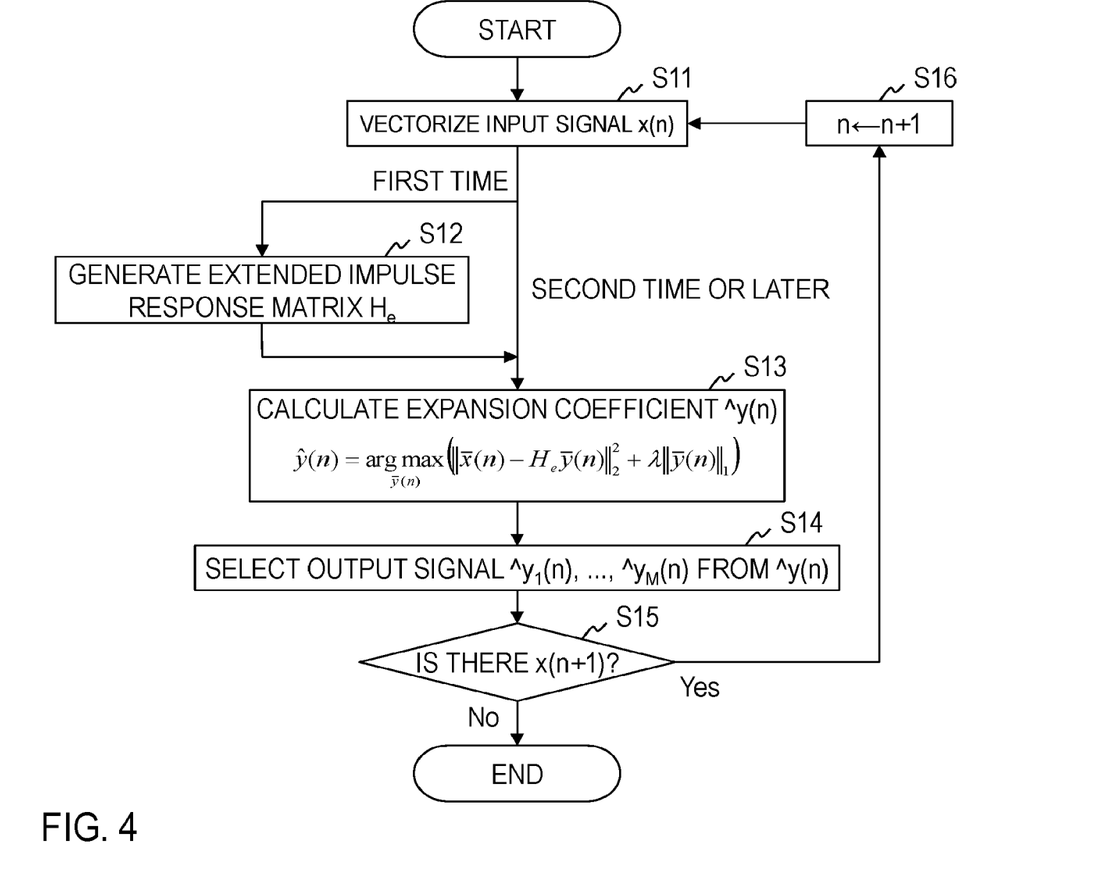
FIG. 4 is a diagram exemplifying a processing procedure of a signal feature extraction method of a first embodiment.

Processing procedure of the signal feature extraction method of the first embodiment will be described with reference to FIG. 4.

In step S11, the signal input part 1 vectorizes an input signal x(n) to be analyzed and generates an input signal vector $\overline{\phantom{x}}x(n)=[x(n+L), \ldots, x(n+1), x(n), x(n-1), \ldots, x(n-L)]^H$. The generated input signal vector $\overline{\phantom{x}}x(n)$ is transmitted to the expansion coefficient calculation part 3.

In step S12, the extended impulse response matrix generation part 2 generates an impulse response vector $\overline{\phantom{h}}h_{m,k}$ that is the formula (10) when k<0 and the formula (11) when k≥0 for m=1, ..., M; k=−2L, ..., −1, 0, 1, ..., 2L, and generates an extended impulse response matrix $H_e$ of $(2L+1)\times M(4L+1)$ which is the formula (12). The generated extended impulse response matrix $H_e$ is transmitted to the expansion coefficient calculation part 3. Because the extended impulse response matrix $H_e$ can be reused for each time n, it may be configured to execute only the first time as shown in FIG. 4.

In step S13, the expansion coefficient calculation part 3 receives the input signal vector $\overline{x}(n)$ from the signal input part 1 and the extended impulse response matrix $H_e$ from the extended impulse response matrix generation part 2, and obtains an expansion coefficient vector $\hat{y}(n)$ by the formula (14). The obtained expansion coefficient vector $\hat{y}(n)$ is transmitted to the signal output part 4.

In step S14, the signal output part 4 receives the expansion coefficient vector $\hat{y}(n)$ from the expansion coefficient calculation part 3 and outputs as an output signal at least one of expansion coefficients $\hat{y}_1(n), \ldots, \hat{y}_m(n), \ldots, \hat{y}_M(n)$ corresponding to center impulse response vectors $\overline{h}_{1,0}, \ldots, \overline{h}_{m,0}, \ldots, \overline{h}_{M,0}$ of the extended impulse response matrix $H_e$ of the expansion coefficient vector $\hat{y}(n)$.

In step S15, it is determined whether there is an input signal x(n+1) at next time (n+1). If there is, 1 is added to a time index n in step S16, and the processing of steps S11 to S14 is performed again. If there is not, the processing is terminated.

Second Embodiment

In the case where only output signals from specific band-pass filters are of interest and output signals of other band-pass filters are not used for analysis explicitly, instead of solving the optimization problem according to the formula (14) as it is, output signals may be generated by using an extended impulse response matrix which is formed by mainly extracting column vectors of interest in the analysis from the extended impulse response matrix $H_e$. If the number of column vectors to be extracted is less than (2L+1), an expansion coefficient vector $\hat{y}(n)$ for the extended impulse response matrix $H_c$ can be obtained as in a formula (15) by a least-squares method in the same manner as the formula (6).

$$\hat{y}(n)=[H_c^H H_c]^{-1} H_c^H \overline{x}(n) \quad (15)$$

What are used as output signals are included in the extended impulse response matrix $H_c$ among the elements of the expansion coefficient vector $\hat{y}(n)$, and in some cases, are only expansion coefficients that correspond to center impulse response vectors $\overline{h}_{1,0}, \ldots, \overline{h}_{m,0}, \ldots, \overline{h}_{M,0}$ and are further limited as main objects of the analysis.

There is a case where waveform patterns greatly different in shape from column vectors of the extended impulse response matrix $H_c$, such as noise, are mixed into the input signal $\overline{x}(n)$ to be analyzed. In the case, after obtaining the expansion coefficient vector $\hat{y}(n)$ like a formula (16) for an input signal vector $\tilde{x}(n)$ obtained by applying filtering processing of removing components having a low correlation with the extended impulse response matrix $H_c$ to the input signal vector $\overline{x}(n)$, an output signal is obtained in the same manner as the first embodiment.

$$\hat{y}(n)=[H_c^H H_c]^{-1} H_c^H \tilde{x}(n) \quad (16)$$

Figure 5:
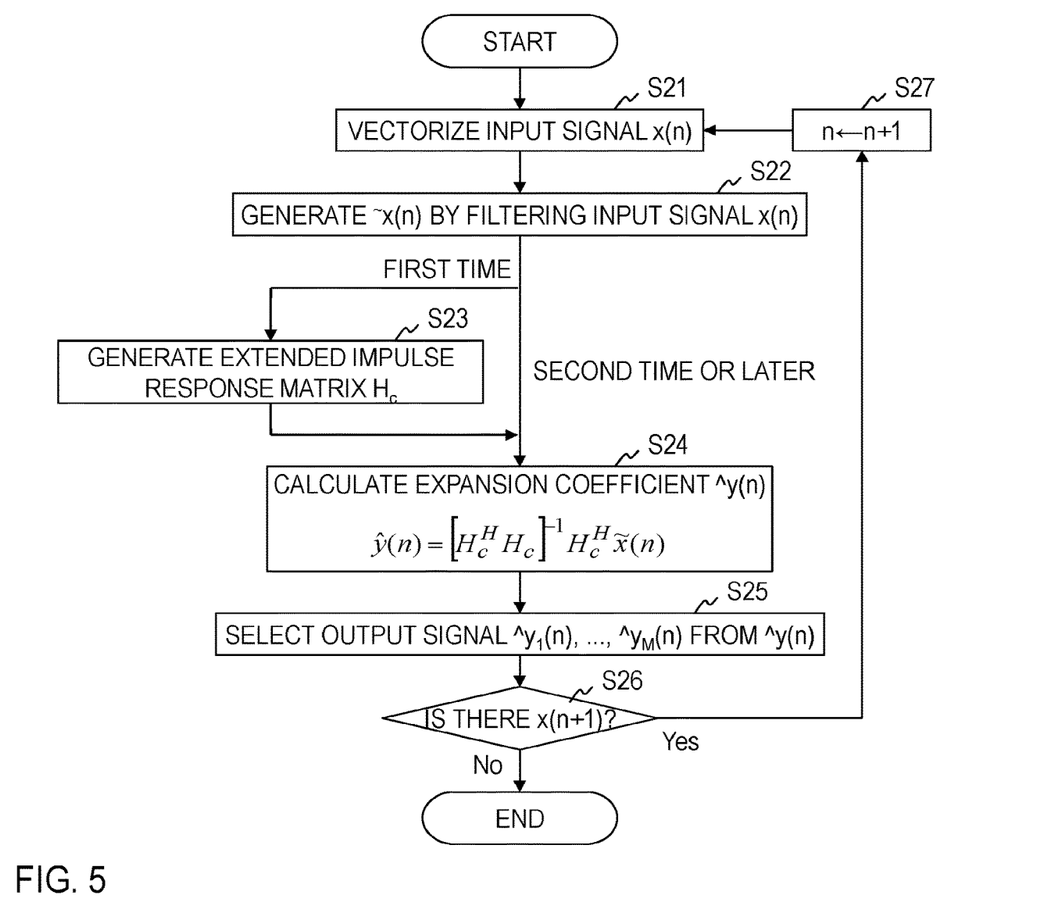
FIG. 5 is a diagram exemplifying a processing procedure of a signal feature extraction method of a second embodiment.

Processing procedure of a signal feature extraction method of the second embodiment will be described with reference to FIG. 5.

In step S21, the signal input part 1 vectorizes all input signal x(n) to be analyzed and generates an input signal vector $\overline{x}(n)$ in the same manner as the first embodiment. In step S22, the signal input part 1 may further apply filtering processing of removing components having a low correlation with the extended impulse response matrix $H_c$ to the input signal vector $\overline{x}(n)$ to generate an input signal vector $\tilde{x}(n)$. It is optional whether the signal input part 1 performs step S22. The generated input signal vector $\overline{x}(n)$ or $\tilde{x}(n)$ is transmitted to the expansion coefficient calculation part 3.

In step S23, the extended impulse response matrix generation part 2 generates an extended impulse response matrix $H_e$ in the same manner as the first embodiment. Furthermore, it generates an extended impulse response matrix $H_c$ by extracting column vectors of interest in analysis from the extended impulse response matrix $H_e$. The column vectors to be extracted are predetermined. The generated extended impulse response matrix $H_c$ is transmitted to the expansion coefficient calculation part 3. Because the extended impulse response matrix $H_c$ can be reused for each time n, it may be configured to execute only the first time as shown in FIG. 5.

In step S24, the expansion coefficient calculation part 3 receives the input signal vector $\overline{x}(n)$ or $\tilde{x}(n)$ from the signal input part 1 and the extended impulse response matrix $H_c$ from the extended impulse response matrix generation part 2, and obtains an expansion coefficient vector $\hat{y}(n)$ by the formula (15) when the input signal vector $\overline{x}(n)$ is received and by the formula (16) when the input signal vector $\tilde{x}(n)$ is received. The obtained expansion coefficient vector $\hat{y}(n)$ is transmitted to the signal output part 4.

In step S25, in the same manner as the first embodiment, the signal output part 4 receives the expansion coefficient vector $\hat{y}(n)$ from the expansion coefficient calculation part 3 and outputs as an output signal at least one of expansion coefficients corresponding to a center impulse response vector $\overline{h}_{m,0}$ of the extended impulse response matrix $H_c$ of the expansion coefficient vector $\hat{y}(n)$.

In step S26, it is determined whether there is an input signal x(n+1) at next time (n+1). If there is, 1 is added to a time index n in step S27, and then the processing of steps S21 to S25 is performed again. If there is not, the processing is terminated.

MODIFIED EXAMPLE

A vector which is a complex conjugate of each column vector of the extended impulse response matrix $H_e$ or $H_c$ may be coupled with the extended impulse response matrix $H_e$ or $H_c$, and then analyzed. Regarding a complex output signal, it may be alright to take a form in which the complex output signal is decomposed into a real part and an imaginary part, or an amplitude component and a phase component, and at least one of them is output. For example, in the cases where distortion is given to a phase characteristic caused by pre-processing such as a high-pass filter or low-pass filter and the waveform of a signal to be analyzed is deformed, or its characteristic pattern is deformed due to individual difference or symptom in an electrocardiogram waveform, an influence of the distortion and deformation can be extracted mainly as a difference in phase components. On the other hand, by observing amplitude components, it is possible to perform common feature extraction (for example, detection of QRS wave and T wave in the electrocardiogram waveform) which is not affected by individual events.

Instead of calculating the formula (14) by using all the column vectors of the extended impulse response matrix $H_e$ of $(2L+1) \times M(4L+1)$ indicated in the formula (12) in the first embodiment, some column vectors are omitted in a range not less than $2L+1$, and a matrix of a smaller size may be used as an extended impulse response matrix.

Furthermore, instead of the following inverse matrixes used in the formulas (15) and (16) in the second embodiment $$[H_c^H H_c]^{-1},$$

it may be calculated by using $$[H_c^H H_c + \delta I]^{-1},$$

where $\delta$ is a positive actual number and I denotes a unit matrix.

With the above configuration, according to the signal feature extraction technique of the invention, leakage of output signals between band-pass filters or in the time axis direction in filter bank analysis is reduced, and therefore it is possible to obtain output signals in which the difference in features of each signal is more clearly shown, which is useful in signal classification and discrimination.

Points of the invention are summarized as follows. In the signal feature extraction method based on the conventional filter bank analysis in which filtering processing is performed independently for each band-pass filter, signal leakage may occur because there is redundancy between band-pass filters and in the time axis direction. In order to prevent this, in the invention, a signal vector is represented by sparse expansion coefficients by over-complete base groups composed of impulse responses of band-pass filters. As a result, it is possible to obtain a result that only outputs of main band-pass filters having a specific feature take a large value and leakage to other band-pass filters is reduced. Obtaining these sparse expansion coefficients corresponds to eliminating mutual redundancy of each band-pass filter.

Because the sparse expansion coefficients are generally high in calculation cost in many cases, in the case where an influence of noise components of no interest in analysis can be excluded beforehand, filtering processing of removing the noise components is applied to the signal to be analyzed to narrow a feature space of the signal, and the expansion coefficients can be obtained under fewer base groups. If the number of base groups can be made smaller than the number of samples of the signal vector to be analyzed, a simple calculation algorithm such as a least-squares method can be applied.

Input signals to be analyzed in the invention are biological signals (for example, an electrocardiogram (ECG, EKG), a pulse wave measured by photoplethysmogram (PPG) or the like, and a respiration curve) related to a physiological phenomenon having arbitrary periodicity including an acoustic signal or heartbeat, pulse, and breathing. The input signals to be analyzed repeat a local waveform pattern having substantially the same size and shape at almost periodic intervals. In addition, there are cases where a plurality of waveform patterns like QRS wave and T wave in the electrocardiogram waveform appear or noise is mixed and observed. The invention contributes to the extraction of features of these signals by outputting large values (peak values) in synchronization with the appearance of a waveform pattern of interest in such signals. In the invention, a measurement method of a biological signal is not questioned. Taking the heartbeat as an example, an object may be an electrocardiogram which is a method for measuring an electric activity associated with the heartbeat or it may be a seismocardiography (SCG) or ballistocardiography (BCG) which measures vibration of skin caused by the heartbeat with an accelerometer. Biological signals not described above may also be included in the analysis objects as long as they have the above characteristics.

Although the embodiments of the present invention have been described above, specific configurations are not limited to these embodiments, and even if design changes and the like are appropriately made without departing from the spirit of the invention, it goes without saying that they are included in the invention. The various processes described in the embodiments may be executed not only in chronological order in accordance with the described order but also in parallel or individually in accordance with processing capability or necessity of an apparatus that executes the processes.

[Program and Recording Medium]

When various processing functions of each apparatus described in the above embodiments are implemented by a computer, processing contents of the functions that each apparatus should have are described by a program. By executing the program by the computer, the various processing functions of each apparatus are implemented on the computer.

The program describing the processing contents can be recorded on a computer-readable recording medium. The computer-readable recording medium may be any medium, for example, a magnetic recording device, an optical disc, a magneto-optical recording medium, and a semiconductor memory.

Distribution of this program is carried out, for example, by selling, transferring, and renting a portable recording medium such as a DVD CD-ROM, or a flash drive in which the program is recorded. Otherwise, the program can be pre-installed in arbitrary recording medium through the manufacturing process in a factory. Furthermore, the program may be stored in a storage device of a server computer, and the program may be distributed by transferring the program from the server computer to another computer via a network.

A computer that executes such a program, for example, stores the program recorded in the portable recording medium or the program transferred from the server computer in its own storage device. When processing is executed, the computer reads the program stored in its own recording medium and executes the processing according to the read program. Furthermore, as another mode of execution of the program, the computer may read the program directory from the portable recording medium and execute processing according to the program, or may sequentially execute, each time a program is transferred from the server computer to the computer, processing according to the received program. In addition, the above-described processing may be executed, not by transferring the program from the server computer to the computer, but by a configuration in which the above-described processing is executed by a so-called ASP (Application Service Provider) type service that achieves a processing function only by giving execution instructions and obtaining results. The program in this form includes information that is used for processing by an electronic computer and conforms to a program (data or the like that is not a direct instruction to a computer but has a characteristic defining processing of the computer).

In this form, the apparatus is configured by executing a predetermined program on a computer, but at least part of the processing contents may be implemented by hardware.

What is claimed is:

1. A signal feature extraction apparatus for extracting features of an input signal by filter bank analysis including a plurality of band-pass filters, assuming that M denotes a number of the band-pass filters, L denotes an integer which a maximum value of impulse response length of the band-pass filters is 2L+1, m denotes each integer from 1 or more to M or less, k denotes each integer from −2L or more to 2L or less, $z_k$ denotes a column vector having |k| zeros as elements, $\overline{x}(n)=[x(n+L), \ldots, x(n+1), x(n), x(n−1), \ldots, x(n−L)]^H$ denotes an input signal vector having an input signal sequence at time n as elements, and $\overline{h}_m = [h_m(−L), \ldots, h_m(−1), h_m(0), h_m(+1), \ldots, h_m(L)]^H$ denotes an impulse response vector having an impulse response sequence of an m-th band-pass filter as elements, the signal feature extraction apparatus comprising:
an extended impulse response matrix generation part that generates an extended impulse response matrix $H_e$ expressed by a following formula $$H_e = [\overline{h}_{1,-2L}, \ldots, \overline{h}_{1,2L}, \ldots, \overline{h}_{m,-2L}, \ldots, \overline{h}_{m,2L}, \ldots, \overline{h}_{M,-2L}, \ldots, \overline{h}_{M,2L}]$$

using an impulse response sequence $\overline{h}_{m,k}$ which is, when k<0, $$\overline{h}_{m,k} = [h_m(−L−k), \ldots, h_m(−1), h_m(0), h_m(1), \ldots, h_m(L), z_k^H]^H,$$

and when k≥0, $$\overline{h}_{m,k} = [z_k^H, h_m(−L), \ldots, h_m(−1), h_m(0), h_m(1), \ldots, h_m(L−k)]^H;$$

an expansion coefficient calculation part that obtains an expansion coefficient vector $\hat{y}(n)$ by calculating a following formula $$\hat{y}(n) = \underset{\overline{y}(n)}{\operatorname{argmax}}(\|\overline{x}(n) - H_e \overline{y}(n)\|_2^2 + \lambda \|\overline{y}(n)\|_1)$$

using the input signal vector $\overline{x}(n)$ and the extended impulse response matrix $H_e$; and a signal output part that outputs as an output signal at least one of expansion coefficients corresponding to a center impulse response vector $\overline{h}_{m,0}$ of the extended impulse response matrix $H_e$ of the expansion coefficient vector $\hat{y}(n)$.

2. A signal feature extraction apparatus for extracting features of an input signal by filter bank analysis including a plurality of band-pass filters, assuming that a superscript H denotes transposition, M denotes a number of the band-pass filters, L denotes a value which a maximum value of impulse response length of the band-pass filters is 2L+1, in denotes each integer from 1 or more to M or less, k denotes each integer from −2L or more to 2L or less, $z_k$ denotes a column vector having |k| zeros as elements, $\overline{x}(n)=[x(n+L), \ldots, x(n+1), x(n), x(n−1), \ldots, x(n−L)]^H$ denotes an input signal vector having an input signal sequence at time n as elements, and $\overline{h}_m = [h_m(−L), \ldots, h_m(−1), h_m(0), h_m(+1), \ldots, h_m(L)]^H$ denotes an impulse response vector having an impulse response sequence of an m-th band-pass filter as elements, the signal feature extraction apparatus comprising:
an extended impulse response matrix generation part that generates an extended impulse response matrix $H_c$ by extracting predetermined column vectors from an extended impulse response matrix $H_e$ expressed by a following formula $$H_e = [\overline{h}_{1,-2L}, \ldots, \overline{h}_{1,2L}, \ldots, \overline{h}_{m,-2L}, \ldots, \overline{h}_{m,2L}, \ldots, \overline{h}_{M,-2L}, \ldots, \overline{h}_{M,2L}]$$

generated by using an impulse response sequence $\overline{h}_{m,k}$ which is, when k<0, $$\overline{h}_{m,k} = [h_m(−L−k), \ldots, h_m(−1), h_m(0), h_m(1), \ldots, h_m(L), z_k^H]^H,$$

and when k≥0, $$\overline{h}_{m,k} = [z_k^H, h_m(−L), \ldots, h_m(−1), h_m(0), h_m(1), \ldots, h_m(L−k)]^H;$$

an expansion coefficient calculation part that obtains an expansion coefficient vector $\hat{y}(n)$ by calculating a following formula $$\hat{y}(n) = [H_c^H H_c]^{-1} H_c^H \overline{x}(n)$$

using the input signal vector $\overline{x}(n)$ and the extended impulse response matrix $H_c$; and a signal output part that outputs as an output signal at least one of expansion coefficients corresponding to a center impulse response vector $\overline{h}_{m,0}$ of the extended impulse response matrix $H_c$ of the expansion coefficient vector $\hat{y}(n)$.

3. The signal feature extraction apparatus according to claim 2, further comprising:

a signal input part that generates an input signal vector $\tilde{x}(n)$ in which components having a low correlation with the extended impulse response matrix $H_c$ are removed from the input signal vector $\overline{x}(n)$, wherein the expansion coefficient calculation part obtains the expansion coefficient vector $\hat{y}(n)$ by calculating a following formula $$\hat{y}(n) = [H_c^H H_c]^{-1} H_c^H \tilde{x}(n)$$

using the input signal vector $\tilde{x}(n)$ and the extended impulse response matrix $H_c$.

4. A signal feature extraction method for extracting features of an input signal by filter bank analysis including a plurality of band-pass filters, assuming that M denotes a number of the band-pass filters, L denotes an integer which a maximum value of impulse response length of the band-pass filters is 2L+1, m denotes each integer from 1 or more to M or less, k denotes each integer from −2L or more to 2L or less, $z_k$ denotes a column vector having |k| zeros as elements, $\overline{x}(n)=[x(n+L), \ldots, x(n+1), x(n), x(n−1), \ldots, x(n−L)]^H$ denotes an input signal vector having an input signal sequence at time n as elements, and $\overline{h}_m = [h_m(−L), \ldots, h_m(−1), h_m(0), h_m(+1), \ldots, h_m(L)]^H$ denotes an impulse response vector having an impulse response sequence of an m-th band-pass filter as elements, the signal feature extraction method comprising:
an extended impulse response matrix generation step in which an extended impulse response matrix generation part generates an extended impulse response matrix $H_e$ expressed by a following formula $$H_e = [\overline{h}_{1,-2L}, \ldots, \overline{h}_{1,2L}, \ldots, \overline{h}_{m,-2L}, \ldots, \overline{h}_{m,2L}, \ldots, \overline{h}_{M,-2L}, \ldots, \overline{h}_{M,2L}]$$

using an impulse response sequence $\bar{h}_{m,k}$ which is,
when k<0, $$\bar{h}_{m,k}=[h_m(-L-k),\ldots,h_m(-1),h_m(0),h_m(1),\ldots,h_m(L),z_k^H]^H,$$

and when $k\geq 0$, $$\bar{h}_{m,k}=[z_k^H,h_m(-L),\ldots,h_m(-1),h_m(0),h_m(1),\ldots,h_m(L-k)]^H;$$

an expansion coefficient calculation step in which an expansion coefficient calculation part obtains an expansion coefficient vector $\hat{y}(n)$ by calculating a following formula $$\hat{y}(n) = \underset{y(n)}{\mathrm{argmax}}(\|\bar{x}(n) - H_e\bar{y}(n)\|_2^2 + \lambda\|\bar{y}(n)\|_1)$$

using the input signal vector $\bar{x}(n)$ and the extended impulse response matrix $H_e$; and a signal output step in which a signal output part outputs as an output signal at least one of expansion coefficients corresponding to a center impulse response vector $\bar{h}_{m,0}$ of the extended impulse response matrix $H_e$ of the expansion coefficient vector $\hat{y}(n)$.

5. A signal feature extraction method for extracting features of an input signal by filter bank analysis including a plurality of band-pass filters, assuming that a superscript H denotes transposition, M denotes a number of the band-pass filters, L denotes a value which a maximum value of impulse response length of the band-pass filters is 2L+1, m denotes each integer from 1 or more to M or less, k denotes each integer from −2L or more to 2L or less, $z_k$ denotes a column vector having |k| zeros as elements, $\bar{x}(n)=[x(n+L),\ldots,x(n+1),x(n),x(n-1),\ldots,x(n-L)]^H$ denotes an input signal vector having an input signal sequence at time n as elements, and $\bar{h}_m=[h_m(-L),\ldots,h_m(-1),h_m(0),h_m(+1),\ldots,h_m(L)]^H$ denotes an impulse response vector having an impulse response sequence of an m-th band-pass filter as elements, the signal feature extraction method comprising:

an extended impulse response matrix generation step in which an extended impulse response matrix generation part generates an extended impulse response matrix $H_c$ by extracting predetermined column vectors from an extended impulse response matrix $H_e$ expressed by a following formula $$H_e=[\bar{h}_{1,-2L},\ldots,\bar{h}_{1,2L},\ldots,\bar{h}_{m,-2L},\ldots,\bar{h}_{m,2L},\ldots,\bar{h}_{M,-2L},\ldots,\bar{h}_{M,2L}]$$

generated by using an impulse response sequence $\bar{h}_{m,k}$ which is,
when k<0, $$\bar{h}_{m,k}=[h_m(-L-k),\ldots,h_m(-1),h_m(0),h_m(1),\ldots,h_m(L),z_k^H]^H,$$

and when $k\geq 0$, $$\bar{h}_{m,k}=[z_k^H,h_m(-L),\ldots,h_m(-1),h_m(0),h_m(1),\ldots,h_m(L-k)]^H;$$

an expansion coefficient calculation step in which an expansion coefficient calculation part obtains an expansion coefficient vector $\hat{y}(n)$ by calculating a following formula $$\hat{y}(n)=[H_c^H H_c]^{-1}H_c^H \bar{x}(n)$$

using the input signal vector $\bar{x}(n)$ and the extended impulse response matrix $H_c$; and a signal output step in which a signal output part outputs as an output signal at least one of expansion coefficients corresponding to a center impulse response vector $\bar{h}_{m,0}$ of the extended impulse response matrix $H_c$ of the expansion coefficient vector $\hat{y}(n)$.

6. The signal feature extraction method according to claim 5, further comprising a signal input step in which a signal input part generates an input signal vector $\tilde{x}(n)$ in which components having a low correlation with the extended impulse response matrix $H_c$ are removed from the input signal vector $\bar{x}(n)$, wherein the expansion coefficient calculation step obtains the expansion coefficient vector $\hat{y}(n)$ by calculating a following formula $$\hat{y}(n)=[H_c^H H_c]^{-1}H_c^H \tilde{x}(n)$$

using the input signal vector $\tilde{x}(n)$ and the extended impulse response matrix $H_c$.

7. A program for causing a computer to function as the signal feature extraction apparatus according to any of claims 1-3.

* * * * *